United States Patent [19]

Kan et al.

[11] Patent Number: 4,914,200

[45] Date of Patent: Apr. 3, 1990

[54] PROCESS FOR PREPARING 4-ACETOXY-3-HYDROXYETHYLAZETIDIN-2-ONE DERIVATIVES

[75] Inventors: Kazunori Kan, Kobe; Noboru Ueyama, Kakogawa; Isao Sada, Akashi; Takehisa Ohashi, Kobe; Kiyoshi Watanabe, Akashi, all of Japan

[73] Assignee: Kanegafuchi Kagaku Kogyo Kabushiki Kaisha, Osaka, Japan

[21] Appl. No.: 309,935

[22] Filed: Feb. 14, 1989

Related U.S. Application Data

[63] Continuation of Ser. No. 43,387, Apr. 28, 1987, abandoned.

[30] Foreign Application Priority Data

Apr. 30, 1986 [JP] Japan ................................ 61-101856
Nov. 13, 1986 [JP] Japan ................................ 61-270622
Feb. 9, 1987 [JP] Japan ................................ 62-28942

[51] Int. Cl.$^4$ ..................... C07D 205/08; C07B 41/12
[52] U.S. Cl. .................................................. 540/357
[58] Field of Search ........................................ 540/357

[56] References Cited

FOREIGN PATENT DOCUMENTS

| | | |
|---|---|---|
| 0070204 | 1/1983 | European Pat. Off. . |
| 0078026 | 5/1983 | European Pat. Off. . |
| 0106652 | 4/1984 | European Pat. Off. . |
| 0167154 | 1/1986 | European Pat. Off. . |
| 0167155 | 1/1986 | European Pat. Off. . |
| 0181831 | 5/1986 | European Pat. Off. . |
| 1770855 | 12/1970 | Fed. Rep. of Germany . |
| 2144419 | 3/1985 | United Kingdom . |

OTHER PUBLICATIONS

Fuchs et al., Chem. Ber. 107, 721–4 (1974).
Yoshida et al., Chemical and Pharmaceutical Bulletin, vol. 29, No. 10, Oct. 1981; pp. 2899–2909.
Shiozaki et al., Tetrahedron, vol. 39, No. 13, 1983, pp. 2399–2407.
Chiba et al., Chemistry Letters, No. 7, 1984, pp. 1927–1930.
Wetter et al., Tetrahedron Letters, vol. 26, No. 45, 1985, pp. 5515–5518.

*Primary Examiner*—Mark L. Berch
*Attorney, Agent, or Firm*—Armstrong, Nikaido, Marmelstein, Kubovcik & Murray

[57] ABSTRACT

A process for preparing a 4-acetoxy-3-hydroxyethylazetidin-2-one derivative having the formula (II):

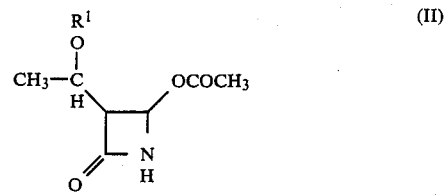

wherein $R^1$ is a protective group for the hydroxyl group, which comprises reacting a β-lactam compound having the formula (I):

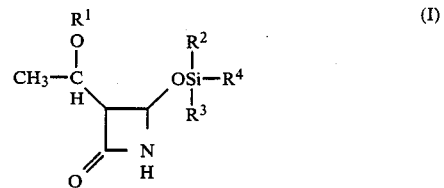

wherein $R^1$ is as defined above, and $R^2$, $R^3$ and $R^4$ are a lower alkyl group having 1 to 6 carbon atoms, phenyl group or an aralkyl group, with acetic anhydride in an organic solvent in the presence of a low concentration of a substituted pyridine. According to the present invention, there can be obtained 4-acetoxy-3-hydroxyethylazetidin-2-one derivatives, which are useful intermediates for preparing carbapenem β-lactam antibiotics.

10 Claims, No Drawings

PROCESS FOR PREPARING 4-ACETOXY-3-HYDROXYETHYLAZETIDIN-2-ONE DERIVATIVES

This application is a continuation of application Ser. No. 043,387 filed Apr. 28, 1987, now abandoned.

BACKGROUND OF THE INNVENTION

The present invention relates to a process for preparing 4-acetoxy-3-hydroxyethylazetidin-2-one derivatives which have a hydroxyethyl group, wherein the hydroxyl group is protected at the C3-position and has an acetoxy group at the C4-position. It is known that 4-acetoxy-3-hydroxyethylazetidin-2-one derivatives are useful intermediates for preparing carbapenem β-lactam antibiotics such as thienamycin and penem β-lactam antibiotics (cf., for example, Tetrahedron Letters by Reider et al., vol. 23, page 2293, 1982 and Chem. Pharm. Bull. by Yoshida et al., vol. 29, page 2899, 1981).

There hitherto have been known processes for synthesizing 4-acetoxy-3-hydroxyethylazetidin-2-one derivatives, for instances, synthesis from 6-aminopenicillanic acid (cf. Chem. Pharm. Bull. by Yoshida et al., vol. 29, page 2899, 1981), synthesis from threonine (cf. Tetrahedron by Shiozaki et al, vol. 39, page 2399, 1983) synthesis from aspartic acid (cf. Tetrahedron Letters by Reider et al., vol. 23, page 2293, 1982) and synthesis from a metal enolate of β-hydroxy butyric acid (cf. Chemistry Letters by Nakai et al., page 1927, 1984). However, these processes have a problem that industrially unfavourable reagents such as mercury compound, e.g., mercury acetate or mercury sulfate and lead tetraacetate are employed in order to introduce an acetoxy group at the C4-position of the β-lactam ring.

The inventors found a process for introducing an acetoxy group at the C4-position by using an N-protected β-lactam compound having an O-protected hydroxyethyl group at the C3-position and a silylether group at the C4-position, and filed a patent application (cf. Japanese Unexamined Patent Publication No. 18758/1986).

However, this process needs two steps, one is to introduce previously a protective group for N of the β-lactam and the other is to remove the protective group after the acetoxy group is introduced at the C4-position.

SUMMARY OF THE INVENTION

The inventors have found a process for introducing the acetoxy group at the C4-position directly without protecting N of the β-lactam, and thus the present invention has been accomplished.

According to the present invention, there is provided a process for preparing a 4-acetoxy-3-hydroxyethylazetidin-2-one derivative having the formula (II):

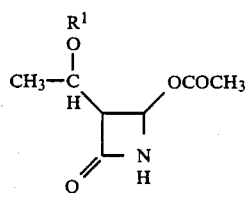

wherein $R^1$ is a protective group for the hydroxy group, which comprises reacting a β-lactam compound having the formula (I):

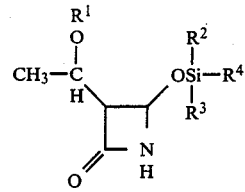

wherein $R^1$ is as defrined above, and $R^2$, $R^3$ and $R^4$ are a lower alkyl group having 1 to 6 carbon atoms, phenyl group or an aralkyl group, with acetic anhydride in an organic solvent in the presence of a low concentration of a substituted pyridine.

DETAILED DESCRIPTION

As shown in the application of the inventors (Japanese Unexamined Patent Publication No. 19791/1986), the β-lactam compound (I) having a silylether group at the C4-position can be easily obtained by the process of the following reaction scheme:

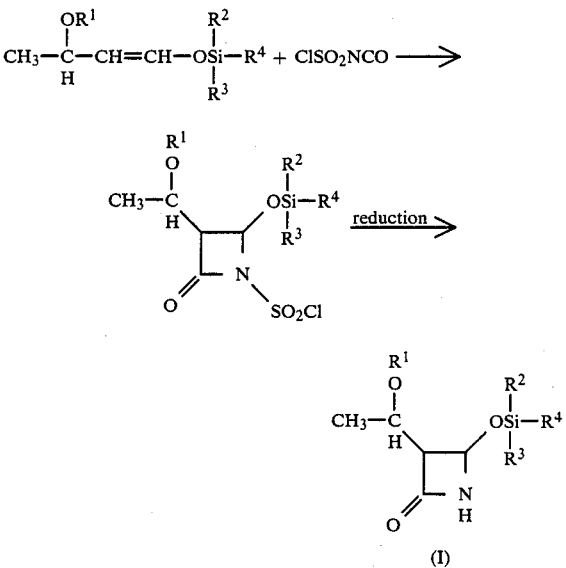

Examples of the O-protective group of $R^1$ for the hydroxyethyl group at the C3-position of the β-lactam compound (I) are, for instance, a trialkylsilyl group having the formula (III):

wherein $R^5$, $R^6$ and $R^7$ are a lower alkyl group having 1 to 6 carbon atoms such as tert-butyldimethylsilyl group, triisopropylsilyl group, isopropyldimethylsilyl group, isobutyldimethylsilyl group, 1,2-dimethylpropyldimethylsilyl group, dimethyl-1,1,2-trimethyl-propylsilyl group, t-butyl group, benzyl group, trichloroethoxycarbonyl group, tert-butoxycarbonyl group, p-nitrobenzyloxycarbonyl group or the like. Among them, the tert-butyldimethylsilyl group, isopropyldimethylsilyl group and dimethyl-1,1,2-trimethylpropylsilyl group are most preferable since they are stable during the reaction and can be selectively removed by acid treatment. $R^2$, $R^3$ and $R^4$ of the β-lactam compound having the formula (I) may be the same or different from each other, and are selected from a lower alkyl group having 1 to 6 carbon atoms such as methyl, ethyl, isopropyl, isobutyl, tert-butyl or 1,1,2-trimethylpropyl group, phenyl group, or an aralkyl group such as benzyl group, p-nitrobenzyl group. It is preferred all of $R^2$, $R^3$ and $R^4$ are methyl group.

The β-lactam compound, prepared as mentioned above, having the formula (I):

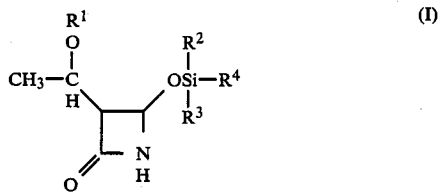

wherein $R^1$, $R^2$, $R^3$ and $R^4$ are as defined above, is reacted with acetic anhydride in an organic solvent in the presence of a low concentration of substituted pyridine to convert the β-lactam compound (I) into the desired 4-acetoxy-3-hydroxyethylazetidin-2-one derivative having the formula (II):

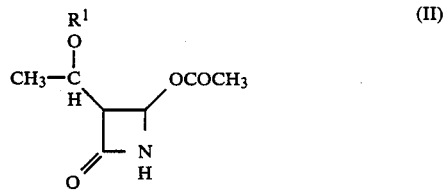

wherein $R^1$ is as defined above. In the above reaction, the concentration of substituted pyridine in the reaction system is an important factor to be considered in order to obtain the desired compound in a sufficient yield, and the most suitable concentration can be decided.

As the substituted pyridine used in the present invention, a dialkylaminopyridine such as 4-dimethylaminopyridine or 4-diethylaminopyridine, and a substituted pyridine, which has a heterocyclic group containing nitrogen atom as substituent, e.g. 4-pyrrolidinopyridine or 4-piperidinopyridine, are preferable. The concentration of the substituted pyridine in the reaction system is preferably in a range of from 0.2 to 3% by weight. When it is lower than 0.2% by weight, the reaction velocity is lowered and the side reaction of substrate decomposition occurs largely. When the concentration is higher than 3% by weight, the yield of by-product having the formula (IV):

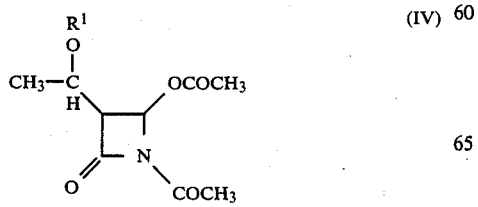

wherein $R^1$ is as defined above, becomes high, and the desired compound cannot be obtained in a sufficient yield.

In the present invention, acetic anhydride is used in a larger amount than that of substituted pyridine, since the reaction velocity is lowered when the amount of acetic anhydride is smaller than that of substituted pyridine. Preferably, acetic anhydride is used in an amount ranging from 10 to 50% by weight in the reaction system. A halogenated hydrocarbon such as methylene chloride or carbon tetrachloride, a hydrocarbon such as n-hexane, an aromatic hydrocarbon such as toluene, ethyl acetate, tetrahydrofuran and tetrahydropyran are preferably employed as a reaction solvent. Pyridine, picoline, lutidine, diethyl ether, diglyme, dimethylformamide, acetone and the like can be also employed as a reaction solvent.

The reaction is carried out at a low temperature in the range from 0° to −70° C. to obtain the desired compound (II) in a sufficient yield. Preferably, the reaction is carried out at a temperature in the range from −10° to −60° C.

The reaction is carried out by dissolving a β-lactam compound (I) having a silyl ether group at the C4-position in an organic solvent such as methylene chloride or toluene, cooling the mixture and then adding acetic anhydride and a substituted pyridine such as 4-dimethylaminopyridine thereto at one time or at several times. And then the reaction is carried out with observing by means of thin layer chromatography, and the reaction mixture is added to water when the starting material disappears or almost disappears. The organic layer is washed with sodium hydrogencarbonate and water, and dried with magnesium sulfate. The solvent is distilled away to obtain a crude crystal, and the desired 4-acetoxy-3-hydroxyethylazetidin-2-one derivative is obtained by means of recrystallization from n-hexane or the like. Also, 4-acetoxy-3-hydroxyethylazetidin-2-one derivatives can be obtained by subjecting the reaction mixture obtained after the evaporation of the solvent to column chromatography.

There has been also found a process for preparing 4-acetoxy-3-hydroxyethylazetidin-2-one derivatives having the formula (II) in a higher yield. That is, the yield of the desired compound is increased by adding a low concentration of water or acetic acid when the β-lactam compound having the formula (I) is reacted with acetic anhydride in an organic solvent in the presence of a low concentration of a substituted pyridine.

The β-lactam compound having the formula (I):

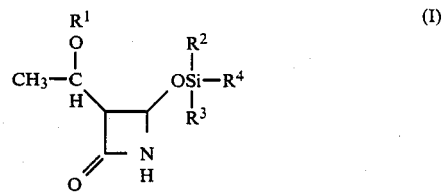

wherein $R^1$, $R^2$, $R^3$ and $R^4$ are as defined above, is subjected to substituted pyridine and acetic anhydride in an organic solvent in the presence of a low concentration of water or acetic acid to convert the β-lactam compound (I) into the desired 4-acetoxy-3-hydroxyethylazetidin-2-one derivative having the formula (II):

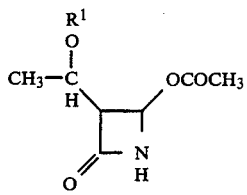

(II)

wherein $R^1$ is as defined above. In the above reaction, the concentration of water or acetic acid in the reaction solvent is an important factor to be considered in order to obtain the desired compound in a sufficient yield, and the most suitable concentration can be decided.

The concentration of water in the reaction solvent is preferably 0.1 to 1.0% by volume. The concentration of acetic acid in the reaction solvent is preferably 0.6 to 5.0% by volume. When the concentration of water or acetic acid is lower than that mentioned above, the yield of by-product having the formula (IV):

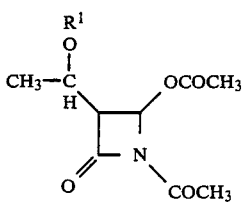

(IV)

wherein $R^1$ is as defined above, becomes high. When the concentration of water or acetic acid is higher than that mentioned above, the side reaction of substrate decomposition occurs largely. Consequently, the desired compound cannot be obtained in a sufficient yield.

As the substituted pyridine used in the present invention, a dialkylaminopyridine such as 4-dimethylaminopyridine or 4-diethylaminopyridine, and a substituted pyridine which has a heterocyclic group containing nitrogen atom as substituent, e.g. 4-pyrrolidinopyridine or 4-piperidinopyridine, are preferable. The concentration of substituted pyridine in the reaction system is preferably in the range of from 0.2 to 3% by weight.

In the present invention, acetic anhydride is used in a larger amount than that of substituted pyridine since the reaction velocity is lowered when the amount of acetic anhydride is smaller than that of substituted pyridine. Preferably, acetic anhydride is used in an amount ranging from 10 to 50% by weight in the reaction system. A halogenated hydrocarbon such as methylene chloride or carbon tetrachloride, a hydrocarbon such as n-hexane, an aromatic hydrocarbon such as toluene, ethyl acetate, tetrahydrofuran and tetrahydropyran are preferably employed as a reaction solvent. Pyridine, picoline, lutidine, diethyl ether, diglyme, dimethylformamide, acetone and the like can be also employed as a reaction solvent.

The reaction is carried out at a low temperature in the range from 0° to −70° C. to obtain the desired compound (II) in a sufficient yield. Preferably, the reaction is carried out at a temperaure in the rane from −10° to −60° C.

The reaction is carried out by dissolving a β-lactam compound (I) having a silyl ether group at the C4-position in an organic solvent such as tetrahydrofuran or ethyl acetate, cooling the mixture, adding a suitable amount of water or acetic acid thereto and then adding acetic anhydride and a substituted pyridine such as 4-dimethylaminopyridine thereto at a temperature mentioned above, at one time or at several times. And then the reaction is carried out with observing by means of thin layer chromatography, and the reaction mixture is added to water when the starting material disappears or almost disappears. The organic layer is washed with sodium hydrogencarbonate and water, and dried with magnesium sulfate. The solvent is distilled away to obtain a crude crystal, and the desired 4-acetoxy-3-hydroxy ethylazetidin-2-one derivative is obtained by means of recrystallization from n-hexane or the like. Also, 4-acetoxy-3-hydroxyethylazetidin-2-one derivatives can be obtained by subjecting the crude crystals to a column chromatography.

The present invention is more specifically explained by the following non-limiting examples. However, it is to be understood that any modification or development can be made without departing from the scope and spirit of the present invention.

EXAMPLE 1

[Preparation of (3R,4R)-4-acetoxy-3-[(R)-1-tert-butyldimethylsilyloxyethyl]azetidin-2-one]

After 157 mg of (3R,4R)-3-[(R)-1-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] was dissolved in 0.9 ml of methylene chloride the mixture was cooled to −35° C. And thereto 544 mg of acetic anhydride and then 20 mg (concentration: 1.05% by weight) of 4-dimethylaminopyridine were added, and the mixture was stirred for one day and night at −35° C. After completion of the rection, there was added a 5% aqueous solution of NaHCO$_3$ and the mixture was separated. The organic layer was washed with water, dried with magnesium sulfate and the solvent was distilled away under reduced pressure to give 147 mg of waxy solid.

The reaction mixture was analyzed by means of high performance liquid column chromatography (column: YMC-pak (A-303 ODS), 4.6×250 mm; column temperature: 50° C.; solvent: methanol/water=7/3 (v/v); flow rate: 1 ml/min.; detection: 210 nm), and 72.5 mg of (3R,4R)-4-acetoxy-3-[(R)-1-tert-butyldimethylsilyloxyethyl]azetidin-2-one was found (yield: 51.0%).

Further, the reaction mixture was dissolved in n-hexane, and the insoluble matter was filtered off. After the mixture was allowed to stand with cooling at −15° C., 44 mg of white solid was obtained. The obtained solid was found to be the desired (3R,4R)-4-acetoxy-3-[(R)-1-tert-butyldimethylsilyloxyethyl]azetidine-2-one, based on following its properties.

$[\alpha]_D^{25} = +50°$ (c=0.5, CHCl$_3$), mp: 107° to 108° C.;
$^1$H-NMR (90 MHz, CDCl$_3$), δ(ppm): 0.08 (6H, s), 0.84 (9H, s), 1.20 (3H, d), 2.10 (3H, s), 3.04 (1H, dd), 4.12 (1H, m), 5.76 (1H, d), 6.73 (NH).

EXAMPLE 2

[Preparation of (3R,4R)-4-acetoxy-3-[(R)-1-tert-butyldimethylsilyloxyethyl]azetidin-2-one]

After 156 mg of (3R,4R)-3-[(R)-1-tert-butyldimethylsilyloxyethyl]-4-trimethylsilyloxyazetidin-2-one was dissolved in 3.6 ml of toluene, the mixture was cooled to −35° C. And thereto 782 g of acetic anhydride and 30 mg (concentration: 0.73% by weight) of 4-dimethylaminopyridine were added, and the mixture was stirred for 43 hours at −35° C. After completion of the reaction and the same treatment as in Example 1, the reaction mixture was analyzed by means of high performance liquid chromatography used in Example and 72 mg of (3R,4R)-4-acetoxy-3-[(R)-1-tert-butyldimethylsilyloxyethyl]azetidin-2-one was found (yield: 51.0%).

The reaction mixture was purified by means of silica-gel column chromatography (hexane:ethyl acetate=10:1) and 65 mg of (3R,4R)-4-acetoxy-3-[(R)-1-tert-butyldimethylsilyloxyethyl]azetidin-2-one was obtained as needles.

EXAMPLES 3 TO 13 AND COMPARATIVE EXAMPLE

[Preparation of (3R,4R)-4-acetoxy-3-[(R)-1-tert-butyldimethylsilyloxyethyl]azetidin-2-one]

Using (3R,4R)-3-[(R)-1-tert-butyldimethylsilyloxyethyl]-4-trimethylsilyloxyazetidin-2-one as a starting material, the reaction was carried out according to the procedure in Example 1 and under the conditions as shown in Table 1 employing 4-dimethylaminopyridine with various concentration, 4-pyrrolidinopyridine or piperidinopyridine as a substituted pyridine, to give (3R,4R)-4-acetoxy-3-[(R)-1-tert-butyldimethylsilyloxyethyl]azetidin-2-one.

The yield was obtained by an analysis with high performance liquid chromatography used in Example 1.

The reaction conditions and yields of the product are shown in Table 1.

TABLE 1

| Ex. No. | reaction solvent | reaction temperature (°C.) | reaction time (Hr) | substituted pyridine concentration (% by weight) | Yield (%) |
| --- | --- | --- | --- | --- | --- |
| 3 | CH$_2$Cl$_2$ | −35 | 23 | dimethylaminopyridine 0.52 | 30 |
| 4 | CH$_2$Cl$_2$ | −35 | 26 | dimethylaminopyridine 0.84 | 38 |
| 5 | CH$_2$Cl$_2$ | −35 | 22 | dimethylaminopyridine 1.14 | 44 |
| 6 | CH$_2$Cl$_2$ | −35 | 24 | dimethylaminopyridine 1.04 | 51 |
| 7 | toluene | −35 | 45 | dimethylaminopyridine 0.73 | 51 |
| 8 | toluene | −35 | 25 | dimethylaminopyridine 1.18 | 40 |
| 9 | ethyl acetate | −35 | 24 | dimethylaminopyridine 1.10 | 50 |
| 10 | CCl$_4$ | −15 | 24 | pyrolidinopyridine 1.10 | 45 |
| 11 | CH$_2$Cl$_2$ | −35 | 22 | piperidinopyridine 0.50 | 42 |
| 12 | toluene | −35 | 24 | dimethylaminopyridine 0.21 | 35 |
| 13 | tetrahydrofuran | −35 | 24 | dimethylaminopyridine 2.95 | 30 |
| Com. Ex. | toluene | −35 | 20 | dimethylaminopyridine 6.3 | 1 |

EXAMPLES 14 AND 15

Using a 4-alkylsilyloxyazetidin-2-one (compound (A)) shown in Table 2 as a starting material, a 4-acetoxyazetidin-2-one (compound (B)) was obtained by means of the same procedure and the same conditions as in Example 1.

The yield of compound (B) are shown in Table 2.

TABLE 2

Compound (A): R$_1$O-substituted isopropyl, OSi–R$_4$ (R$_2$, R$_3$) azetidin-2-one $$\text{(A)} \xrightarrow[\text{CH}_2\text{Cl}_2, -35°\text{C., overnight}]{\text{4-dimethylaminopyridine/acetic anhydride}} \text{(B)}$$

Compound (B): R$_1$O-substituted isopropyl, OCOCH$_3$ azetidin-2-one

| Ex. No. | Compound (A) | Concentration of 4-dimethylaminopyridine (% by weight) | Yield of compound (B) (%) |
| --- | --- | --- | --- |
| 14 | R$_1$ = Si(CH$_3$)$_2$—C(CH$_3$)$_2$—CH(CH$_3$)$_2$<br>R$_2$, R$_3$, R$_4$ = CH$_3$ | 1.1 | 51 |
| 15 | R$_1$ = Si(CH$_3$)$_2$—CH(CH$_3$)$_2$<br>R$_2$, R$_3$, R$_4$ = CH$_3$ | 1.1 | 40 |

EXAMPLE 16

[Preparation of (3R,4R)-4-acetoxy-3-[(R)-1-tert-butyldimethylsilyloxyethyl]azetidin-2-one]

After 157 mg of (3R,4R)-3-[(R)-1-tert-butyldimethylsilyloxyethyl]-4-trimethylsilyloxyazetidin-2-one was dissolved in 1.6 ml of tetrahydrofuran, the mixture was cooled to −35° C. And thereto 0.005 ml (concentration; 0.31% by volume) of water, 0.5 ml of acetic anhydride and then 20 mg (concentration: 0.93% by weight) of 4-dimethylaminopyridine were added, and the mixture was stirred for 22 hours at −35° C. After completion of the reaction, there were added ethyl acetate and 5% aqueous solution of NaHCO$_3$, and the mixture was separated. The organic layer was washed with water and the solvent was distilled away under reduced pressure to give 14 mg of solid.

The reaction mixture was analyzed by means of high performance liquid chromatography (column: YMC-pak (A-303 ODS), 4.6×250 nm, column temperature 15° C., solvent: CH$_3$CN/water=6/4 (v/v), flow rate: 1 ml/min., direction: 210 nm) to find 99.5 mg of (3R,4R)-4-acetoxy-3-[(R)-1-tert-butyldimethylsilyloxyethyl]azetidin-2-one (yield: 70%).

Further, the reaction mixture was dissolved in n-hexane, and the insoluble matter was filtered off. After the mixture was allowed to stand with cooling at −15° C., 89 mg of white solid was obtained. The obtained solid was found to be the desired (3R,4R)-4-acetoxy-3-[(R)-1-tert-butyldimethylsilyloxyethyl]azetidin-2-one, based on following its properties.

$[\alpha]_D^{25} = +50°$ (c=0.5, CHCl$_3$), mp=107° to 108° C.;
$^1$H-NMR (90 MHz CDCl$_3$), δ(ppm): 0.08 (6H, s), 0.84 (9H, s), 1.20 (3H, d), 2.10 (3H, s), 3.04 (1H, dd), 4.12 (1H, m), 5.76 (1H, d), 6.78 (NH).

EXAMPLE 17

[Preparation of (3R,4R)-4-acetoxy-3-[(R)-1-tert-butyldimethylsilyloxyethyl]azetidin-2-one]

After 156 mg of (3R,4R)-3-[(R)-1-tert-butyldimethylsilyloxyethyl]-4-trimethylsilyloxyazetidin-2-one was dissolved in 1.6 ml of ethyl acetate, the mixture was cooled to −35° C. And thereto 0.005 ml (concentration: 0.31% by volume) of water, 0.5 ml of acetic anhydride and then 30 mg (concentration: 1.38% by weight) of 4-dimethylaminopyridine were added. The mixture was stirred for 21 hours at −35° C. After completion of the reaction and the same treatment as in Example 16, it was analyzed by means of high performance liquid chromatography used in Example 16 to find 85 mg of (3R,4R)-4-acetoxy-3-[(R)-1-tertbutyldimethylsilyloxyethyl]azetidin-2-one (yield: 60%). By recrystallization from n-hexane, 76 mg of the above compound was obtained as needles.

EXAMPLE 18

[Preparation of (3R,4R)-4-acetoxy-3-[(R)-1-tert-butyldimethylsilyloxyethyl]azetidin-2-one]

After 156 mg of (3R,4R)-3-[(R)-1-tert-butyldimethylsilyloxyethyl]-4-trimethylsilyloxyazetidin-2-one was dissolved in 1.6 ml of ethyl acetate, the mixture was cooled to −35° C. and thereto 0.03 ml (concentration: 1.84% by volume) of acetic acid, 0.5 ml of acetic anhydride and then 30 mg (concentration: 1.36% by weight) of 4-dimethylaminopyridine were added. The mixture was stirred for 21 hours at −35° C. After completion of the reaction and the same treatment as in Example 16, it was analyzed by means of high performance liquid chromatography used in Example 16 to find 83 mg of (3R,4R)-4-acetoxy-3-[(R)-1-tert-butyldimethylsilyloxyethyl]azetidin-2-one (yield: 59%).

EXAMPLE 19

[Preparation of (3R,4R)-4-acetoxy-3-[(R)-1-tert-butyldimethylsilyloxyethyl]azetidin-2-one]

After 155 mg of (3R,4R)-3-[(R)-1-tert-butyldimethylsilyloxyethyl]-4-trimethylsilyloxyazetidin-2-one was dissolved in 1.6 ml of tetrahydrofuran, the mixture was cooled to −35° C. And thereto 0.03 ml (concentration: 1.84% by volume) of acetic acid, 0.5 ml of acetic anhydride and then 20 mg (concentration: 0.92% by weight) of 4-dimethylaminopyridine were added. The mixture was stirred for 22 hours at −35° C. After the same treatment as in Example 16, it was analyzed by means of high performance liquid chromatography used in Example 16 to find 84 mg of (3R,4R)-4-acetoxy-3-[(R)-1-tert-butyldimethylsilyloxyethyl]azetidin-2-one (yield: 60%).

EXAMPLE 20

[Preparation of (3R,4R)-4-acetoxy-3-[(R)-1-tert-butyldimethylsilyloxyethyl]azetidin-2-one]

The procedures in Example 16 were repeated except that 0.01 ml (concentration: 0.62% by volume) of water was used instead of 0.005 ml of water. In the reaction system, the concentration of 4-dimethylaminopyridine was 0.93% by weight.

The yield of the obtained (3R,4R)-acetoxy-3-[(R)-1-tert-butyldimethylsilyloxyethyl]azetidin-2-one was 65%.

EXAMPLE 21

[Preparation of (3R,4R)-4-acetoxy-3-[(R)-1-tert-butyldimethylsilyloxyethyl]azetidin-2-one]

The procedures in Example ≠were repeated except that 0.06 ml (concentration: 3.6% by volume) of acetic acid was used instead of 0.005 ml of water. In the reaction system, the concentration of 4-dimethylaminopyridine was 0.91% by weight.

The yield of the obtained (3R,4R)-4-acetoxy-3-[(R)-1-tert-butyldimethylsilyloxyethyl-azetidin-2-one was 66%.

EXAMPLES 22 TO 24

Using a 4-alkylsilyloxyazetidin-2-one (compound (A)) shown in Table 3 as a starting material, a 4-acetoxyazetidin-2-one (compound (B)) was obtained after the same reaction and treatment as in Example 17.

The yields are shown in Table 3.

TABLE 3

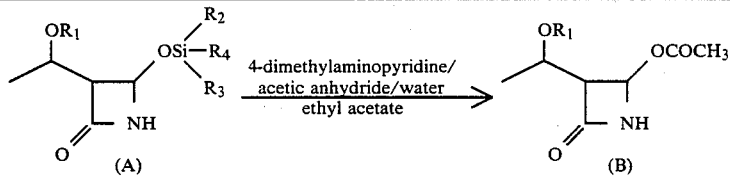

| Ex. No. | Compound A | Concentration of 4-dimethylaminopyridine (% by weight) | Concentration of H$_2$O (% by volume) | yield of compound (B) (%) |
|---|---|---|---|---|
| 22 | R$_1$ = Si(CH$_3$)$_2$C(CH$_3$)$_2$—CH(CH$_3$)$_2$<br>R$_2$, R$_3$, R$_4$ = CH$_3$ | 1.4 | 0.31 | 60 |
| 23 | R$_1$ = Si(CH$_3$)$_2$—CH(CH$_3$)$_2$<br>R$_2$, R$_3$, R$_4$ = CH$_3$ | 1.3 | 0.32 | 50 |
| 24 | R$_1$ = Si(CH$_3$)$_2$—(CH(CH$_3$)—CH(CH$_3$)$_2$<br>R$_2$, R$_3$, R$_4$ = CH$_3$ | 1.3 | 0.31 | 50 |

EXAMPLE 25

[Preparation of
(3R,4R)-4-acetoxy-3-[(R)-1-tert-butyldimethylsilyloxyethyl]azetidin-2-one]

After 311.3 mg of (3R,4R)-3-[(R)-1-tert-butyldimethylsilyloxyethyl-4-trimethylsilyloxyazetidin-2-one was dissolved in 3.2 ml of pyridine, the mixture was cooled to −50° C. And thereto 0.3 ml of acetic anhydride, 30 mg (concentration: 0.79% by weight) of 4-dimethylaminopyridine and 0.01 ml (concentration: 0.31% by volume) of water were added, and the mixture was stirred for 18.5 hours at −50° C. After completion of the reaction, there were added hexane and a buffer solution consisting of citric acid and sodium hydrogencarbonate and the mixture was separated. The organic layer was washed with water and the solvent was distilled away under reduced pressure to give 294.9 mg of solid. The obtained solid was analyzed by means of the same procedure as in Example 16 to find 180 mg of (3R,4R)-4-acetoxy-3-[(R)-1-tert-butyldimethylsilyloxyethyl]azetidin-2-one (yield: 64%).

EXAMPLES 26 TO 31

[Preparation of
(3R,4R)-4-acetoxy-3-[(R)-1-tert-butyldimethylsilyloxyethyl]azetidin-2-one]

The procedures in Example 16 were repeated except that a solvent and its amount shown in Table 4 was used instead of 1.6 ml of tetrahydrofuran.

The yields of obtained (3R,4R)-4-acetoxy-3-[(R)-1-tert-butyldimethylsilyloxyethyl]azetidin-2-one and the concentration of 4-dimethylaminopyridine are shown in Table 4.

TABLE 4

| Ex. No. | solvent and its amount (ml) | concentration of 4-dimethylaminopyridine (% by weight) | concentration of H₂O (% by volume) | yield (%) |
|---|---|---|---|---|
| 26 | dimethylformamide 1.6 | 0.90 | 0.31 | 55 |
| 27 | diethylether 1.6 | 1.1 | 0.31 | 43 |
| 28 | acetone 1.6 | 1.0 | 0.31 | 48 |
| 29 | diglyme 1.6 | 0.90 | 0.31 | 44 |
| 30 | methylene chloride 1.6 | 0.70 | 0.31 | 50 |
| 31 | toluene 1.6 | 0.95 | 0.31 | 45 |

EXAMPLE 32

[Preparation of
(3R,4R)-4-acetoxy-3-[(R)-1-tert-butyldimethylsilyloxyethyl]azetidin-2-one After 300 mg of (3R,4R)-3-[(R)-1-tert-butyldimethylsilyloxyethyl]-4-trimethylsilyloxyazetidin-2-one was dissolved in 1 ml of tetrahydrofuran, the mixture was cooled to −55° C. And thereto 0.005 ml (concentration: 0.5% by volume) of water, 0.8 ml of acetic anhydride and then 35 mg (concentration: 1.67% by weight) of 4-dimethylaminopyridine were added, and the mixture was stirred for 69 hours at −55° C. After completion of the reaction, there were added 20 ml of ethyl acetate and 20 ml of 5% aqueous solution of NaHCO₃ and the mixture was separated. The organic layer was washed with water, dried with magnesium sulfate and the solvent was distilled away under reduced pressure to give 265 mg of solid.

The reaction mixture was analyzed by using a high performance liquid chromatography (column: YMC-pak (A-303 ODS), 4.6×250 mm; column temperature: 15° C.; solvent: CH₃CN/water=6/4 (v/v); flow rate: 1 ml/min; detection: 210 nm) to find 212 mg of (3R,4R)-4-acetoxy-3-[(R)-1-tert-butyldimethylsilyloxyethyl]azetidin-2-one (yield: 78%).

EXAMPLE 33

[Preparation of
(3R,4R)-4-acetoxy-3-[(R)-1-tert-butyldimethylsilyloxyethyl]azetidin-2-one]

The procedures in Example 16 were repeated except that water was not added. The concentration of 4-dimethylaminopyridine was 0.94% by weight.

The yield of the obtained (3R,4R)-4-acetoxy-3-[(R)-1-tert-butyldimethylsilyloxyethyl]azetidin-2-one was 40%.

EXAMPLE 34

[Preparation of
(3R,4R)-4-acetoxy-3-[(R)-1-tert-butyldimethylsilyloxy]azetidin-2-one]

The procedures in Example 17 were repeated except that water was not added. The concentration of 4-dimethylaminopyridine was 1.38% by weight.

The yield of the obtained (3R,4R)-4-acetoxy-3-[(R)-1-tert-butyldimethylsilyloxy]azetidin-2-one was 40%.

EXAMPLE 35

[Preparation of
(3R,4R)-4-acetoxy-3-[(R)-1-tert-butyldimethylsilyloxy]azetidin-2-one]

The procedures in Example 17 were repeated except that 0.05 ml (concentration: 3.03% by volume) of water was used instead of 0.005 ml of water. The concentration of 4-dimethylaminopyridine was 1.35% by weight.

The yield of the obtained (3R,4R)-4-acetoxy-3-[(R)-1-tert-butyldimethylsilyloxy]azetidin-2-one was 35%.

EXAMPLE 36

[Preparation of
(3R,4R)-4-acetoxy-3-[(R)-1-tert-butyldimethylsilyloxy]azetidin-2-one]

The procedures in Example 19 were repeated except that 0.15 ml (concentration: 8.57% by volume) of acetic acid was used instead of 0.03 ml of acetic acid. The concentration of 4-dimethylaminopyridine was 1.29% by weight.

The yield of the obtained (3R,4R)-4-acetoxy-3-[(R)-1-(tert-butyldimethylsilyloxy)ethyl]azetidin-2-one was 37%.

In addition to the ingredients used in the Examples, other ingredients can be used in the Examples as set forth in the specification to obtain substantially the same results.

What we claim is:

1. A process for preparing a 4-acetoxy-3-hydroxyethylazetidin-2-one derivative having the formula (II):

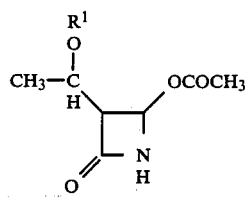 (II)

wherein $R^1$ is a protective group for the hydroxyl group, which comprises reacting a β-lactam compound having the formula (I):

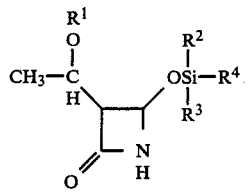 (I)

wherein $R^1$ is as defined above, and each of $R^2$, $R^3$ and $R^4$ is independently a lower alkyl group having 1 to 6 carbon atoms, phenyl group or an aralkyl group, with acetic anhydride in an organic solvent containing water in an amount of from 0.1% to 1.0% by volume or containing acetic acid in an amount of from 0.6% to 5.0% by volume in the presence of a dialkylaminopyridine, 4-pyrrolidinopyridine or 4-piperidinopyridine at a temperature ranging from 0° C. to −70° C., the concentration of said acetic anhydride being from 10% to 50% by weight and the concentration of said dialkylaminopyridine, 4-pyrrolidinopyridine or 4-piperidinopyridine being from 0.2% to 3% by weight in the reaction system.

2. A process for preparing a 4-acetoxy-3-hydroxyethylazetidin-2-one derivative having the formula (II):

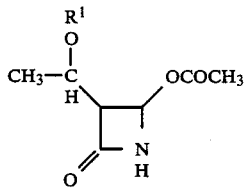 (II)

wherein $R^1$ is a protective group for the hydroxyl group, which comprises reacting a β-lactam compound having the formula (I):

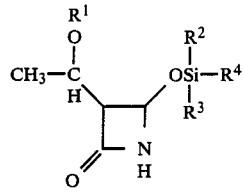 (I)

wherein $R^1$ is as defined above, and each of $R^2$, $R^3$ and $R^4$ is independently a lower alkyl group having 1 to 6 carbon atoms, phenyl group or an aralkyl group, with acetic anhydride in an organic solvent in the presence of a dialkylaminopyridine, 4-pyrrolidinopyridine or 4-piperidinopyridine at a temperature ranging from −35° C. to −70° C.; the concentration of said acetic anhydride being from 10% to 50% by weight and the concentration of said dialkylaminopyridine, 4-pyrrolidinopyridine or 4-piperidinopyridine being from 0.2% to 3.0% by weight.

3. The process of claim 1, wherein $R^1$ is a group of the formula (III):

 (III)

wherein each of $R^5$, $R^6$ and $R^7$ is a lower alkyl group having 1 to 6 carbon atoms.

4. The process of claim 1, wherein $R^1$ is t-butyldimethylsilyl group.

5. The process of claim 1, wherein $R^1$ is isopropyldimethylsilyl group.

6. The process of claim 1, wherein $R^1$ is dimethyl-1,1,2-trimethylpropylsilyl group.

7. The process of claim 1 wherein $R^2$, $R^3$ and $R^4$ are methyl groups.

8. The process of claim 1, wherein said dialkylaminopyridine is 4-dimethylaminopyridine.

9. The process of claim 1, wherein said organic solvent is tetrahydrofuran.

10. The process of claim 1, wherein said organic solvent is pyridine.

* * * * *